(12) United States Patent  
Zeiger et al.

(10) Patent No.: US 8,875,055 B1
(45) Date of Patent: Oct. 28, 2014

(54) INTERFACE FOR CREATING AND VIEWING MEDICAL DECISION SUPPORT RULES

(75) Inventors: Roni F. Zeiger, Mountain View, CA (US); Arthur E. Blume, Melrose, MA (US)

(73) Assignee: Google Inc., Mountain View, CA (US)

( * ) Notice: Subject to any disclaimer, the term of this patent is extended or adjusted under 35 U.S.C. 154(b) by 931 days.

(21) Appl. No.: 12/324,973

(22) Filed: Nov. 28, 2008

(51) Int. Cl.
    *G06F 3/048* (2013.01)

(52) U.S. Cl.
    USPC ............ 715/835; 715/262; 715/780; 715/846

(58) Field of Classification Search
    USPC .......... 715/262, 267, 270, 780, 835, 967, 846
    See application file for complete search history.

(56) References Cited

U.S. PATENT DOCUMENTS

| | | | | |
|---|---|---|---|---|
| 5,276,795 A * | 1/1994 | Hoeber et al. | ................. | 715/813 |
| 5,574,828 A * | 11/1996 | Hayward et al. | ................. | 706/45 |
| 5,596,752 A * | 1/1997 | Knudsen et al. | ............... | 717/117 |
| 5,715,449 A * | 2/1998 | Peters et al. | ............................ | 1/1 |
| 5,909,678 A * | 6/1999 | Bergman et al. | ....................... | 1/1 |
| 5,963,938 A * | 10/1999 | Wilson et al. | ........................... | 1/1 |
| 6,137,488 A * | 10/2000 | Kraft et al. | ..................... | 715/866 |
| 6,983,423 B2 | 1/2006 | Dvorak et al. | | |
| 7,085,757 B2 * | 8/2006 | Dettinger et al. | ..................... | 1/1 |
| 7,213,009 B2 * | 5/2007 | Pestotnik | ........................ | 706/46 |
| 7,251,610 B2 | 7/2007 | Alban et al. | | |
| 7,275,220 B2 | 9/2007 | Brummel et al. | | |
| 7,337,123 B2 | 2/2008 | Dvorak et al. | | |
| 2004/0215612 A1* | 10/2004 | Brody | ................................. | 707/3 |
| 2005/0004911 A1* | 1/2005 | Goldberg et al. | .................. | 707/7 |
| 2005/0192953 A1* | 9/2005 | Neale et al. | ......................... | 707/4 |
| 2006/0047552 A1 | 3/2006 | Larsen et al. | | |
| 2006/0047553 A1 | 3/2006 | Fuhrmann et al. | | |
| 2006/0106745 A1* | 5/2006 | Armstrong et al. | ............. | 706/47 |
| 2006/0117021 A1 | 6/2006 | Sidney et al. | | |
| 2006/0161468 A1 | 7/2006 | Larsen et al. | | |
| 2006/0271408 A1* | 11/2006 | Rosenfeld et al. | ................ | 705/3 |
| 2008/0201313 A1* | 8/2008 | Dettinger et al. | ................. | 707/4 |

* cited by examiner

*Primary Examiner* — Kieu Vu

*Assistant Examiner* — Aaron Lowenberger

(74) *Attorney, Agent, or Firm* — Brake Hughes Bellermann, LLP

(57) ABSTRACT

A first statement of a rule and a first icon associated with the first statement are displayed. A user's selection of the first icon is received, and the selection of a Boolean operator is received in association with the selection. A second statement is displayed, and a link between the first statement and the second statement is displayed to form a compound statement including the first and second statements. The link includes an indication of the Boolean operator selected by the user. A second icon is displayed in association with the second statement, where the second icon is selectable by the user to allow selection of Boolean operators with which the user may link the second statement to a third statement. A third icon is displayed in association with the compound statement, where the icon is selectable by the user to allow selection of a Boolean operator to link the compound statement to a third statement.

18 Claims, 9 Drawing Sheets

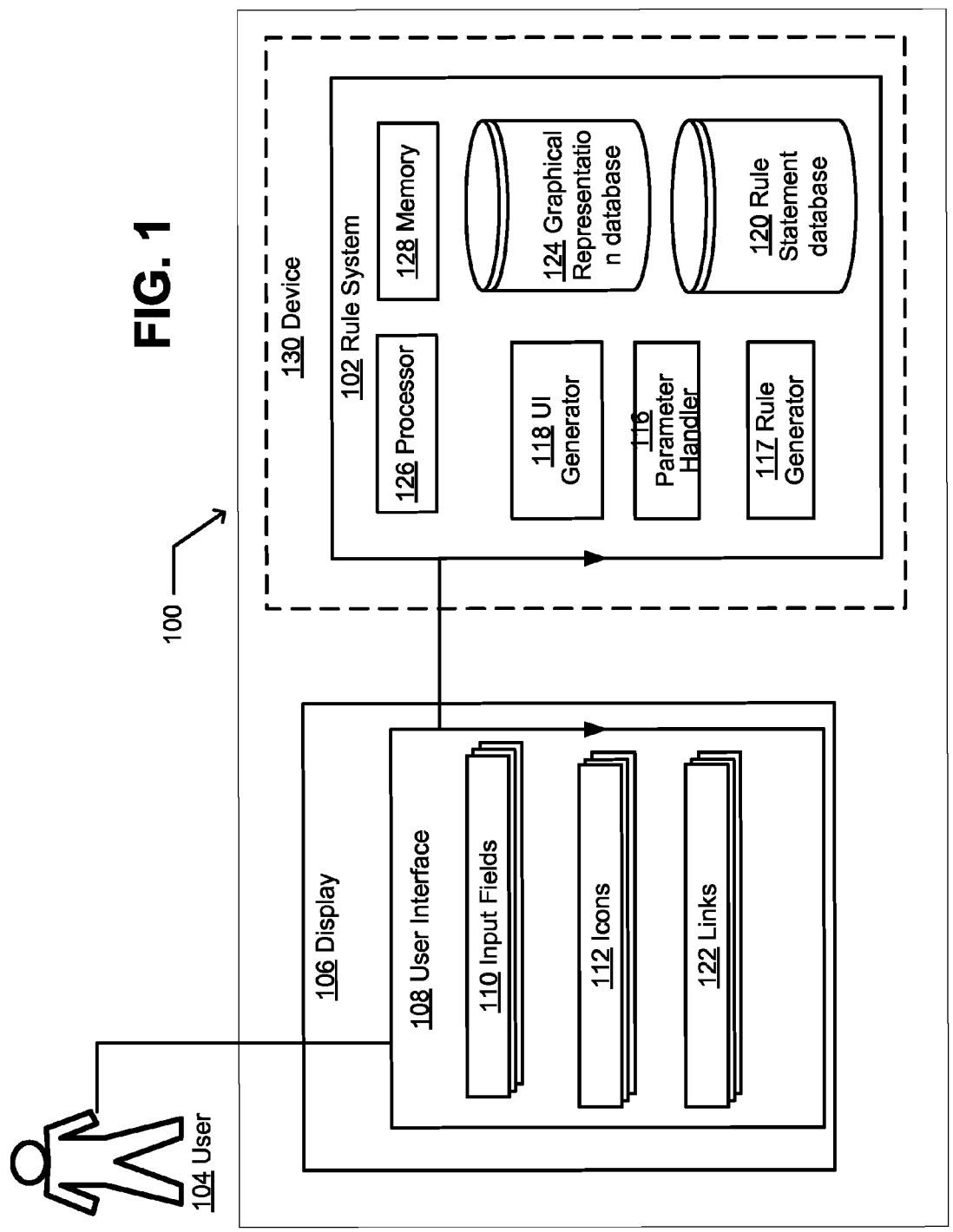

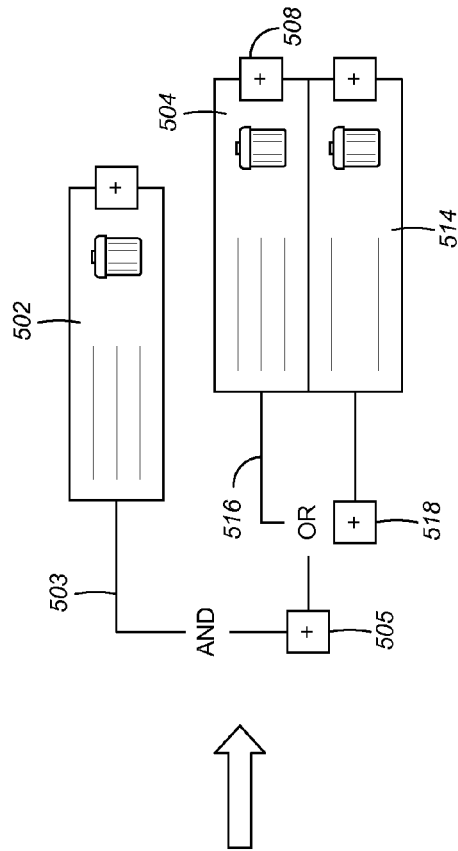
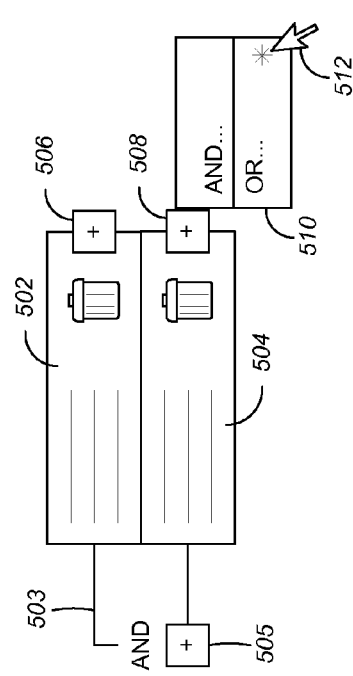
FIG. 5B
FIG. 5A

INTERFACE FOR CREATING AND VIEWING MEDICAL DECISION SUPPORT RULES

TECHNICAL FIELD

This description relates to an interface for generating Boolean rules and, in particular, to an interface for creating and viewing medical decision support rules.

BACKGROUND

Rule-based systems are increasingly used to determine diagnoses and treatments in a variety of settings, e.g., in medicine, manufacturing, business, government. For example, in a clinical setting, adhering to a rule-based system may ensure that a patient with a severe allergy to penicillin is not given a drug in the same family as penicillin, or that a 40 year old woman is reminded to get an annual pap smear for cervical cancer screening. Typically, technical personnel must create and maintain the systems that encode and enforce these rules, but domain experts (e.g., medical doctors, shop foremen, business executives, and government supervisors) must write and maintain the content of these rules. Many systems are not user-friendly enough for domain experts to use effectively—both initially and over time to keep a rule-based system up-to-date. Indeed, having an out-of-date rule can pose a safety and legal threat to a health care provider using the out-of-date rule in a decision support system.

SUMMARY

In a first general aspect, a computer-implemented method includes displaying a first statement of a rule and displaying a first icon in association with the first statement. A user's selection of the first icon is received, and the user's selection of a Boolean operator is received in association with the user's selection of the first icon. A second statement of the rule is displayed, and a link between the first statement and the second statement is displayed to form a compound statement including the first and second statements, where the link includes an indication of the Boolean operator selected by the user. A second icon is displayed in association with the second statement, where the second icon is selectable by the user to allow the user to select a Boolean operators with which the user may link the second statement via the selected Boolean operator to a third statement. A third icon is displayed in association with the compound statement, where the icon is selectable by the user to allow the user to select a Boolean operator with which the user may link the compound statement to a third statement.

Implementations may include one or more of the following features. For example, in association with the user's selection of the first icon, a selectable choice can be displayed to the user of the Boolean operators, AND and OR. A first position of an icon relative to a statement can indicate that the icon may be selected by the user to link the statement to another statement, and a second position of the icon relative to a compound statement can indicate that the icon may be selected by the user to link the compound statement to another statement. The first position can be on a first side of the statement and the second position can be on a second side of the compound statement. Representations of the first, second, and third icon can be substantially similar.

A fourth icon can be displayed in association with the first statement, where the fourth icon is selectable by the user to undisplay the first statement, and a fifth icon can be displayed in association with the second statement. The rule can be stored in a memory, and then the rule can be submitted to a quality assurance reviewer, feedback can be received from the quality assurance reviewer, and whether to approve the rule for use by other users based on the feedback from the quality assurance reviewer can be determined.

The rule can include a plurality of eligibility statements and/or compliance statements. The first and second statements of the rule can include one or more sub-statements selected by the user from a controlled vocabulary of statements concerning a medical condition or treatment of a patient.

A user's selection of the third icon can be received, and the user's selection of a Boolean operator can be received, in association with the user's selection of the third icon. A third statement of the rule can be received, and a link between the third statement and the compound statement of the first and second statements can be displayed, where the link includes an indication of the Boolean operator selected by the user that logically links the third statement and the compound statement of the first and second statements, and where the second link logically links the first compound statement and the third statement of the rule to form a second compound statement.

In another general aspect, a computer program product tangibly embodied in a machine-readable medium can include executable instructions that, when executed, are configured to cause one or more data processing apparatuses to display a first statement of a rule, display a first icon in association with the first statement, receive a user's selection of the first icon, receive the user's selection of a Boolean operator in association with the user's section of the first icon, display a second statement of the rule, and display a link between the first statement and the second statement to form a compound statement including the first and second statements, where the link includes an indication of the Boolean operator selected by the user. Execution of the instructions also can cause the one or more data processing apparatuses to display a second icon in association with the second statement, where the second icon is selectable by the user to allow the user to select a Boolean operator with which the user may link the second statement via the selected Boolean operator to a third statement; and to display a third icon in association with the compound statement, where icon is selectable by the user to allow the user to select a Boolean operator with which the user may link the compound statement to a third statement.

Implementations may include one or more of the following features. For example, executable instructions also can be included that, when executed, cause the data processing apparatuses to display, in association with the user's selection of the first icon, a selectable choice to the user of the Boolean operators, AND and OR. Executable instructions also can be included that, when executed, cause the data processing apparatuses to display a fourth icon in association with the first statement, where the fourth icon is selectable by the user to undisplay the first statement and to display a fifth icon in association with the second statement. Executable instructions also can be included that, when executed, cause the data processing apparatuses to display a field for inputting a sub-statement of the first statement, to receive input from the user in the field, based on the input, to display a choice of a plurality of sub-statements for selection by the user as the sub-statement of the first statement, and to receive a selection from the user of one of the plurality of sub-statements for use as the sub-statement of the first statement. Executable instructions also can be included that, when executed, cause the data processing apparatuses to display a field for inputting a sub-statement of the first statement, to receive input from the user in the field, to compare the input to a plurality of pre-determined sub-statements, wherein the sub-statements are stored in a database, if the input does not match a pre-determined sub-statement, then to submit the input to a quality assurance reviewer and to receive feedback from the quality assurance reviewer, and to determine whether to approve the input for use as pre-determined sub-statement based on the feedback from the quality assurance reviewer.

Executable instructions also can be included that, when executed, cause the data processing apparatuses to receive a user's selection of the third icon, to receive the user's selection of a Boolean operator in association with the user's selection of the third icon, to display a third statement of the rule, and to display a second link between the third statement and the compound statement of the first and second statements, where the second link includes an indication of the Boolean operator selected by the user in association with the user's selection of the third icon, and where the second link logically links the compound statement of the first and second statements to the third statement of the rule to form a second compound statement. Executable instructions also can be included that, when executed, cause the data processing apparatuses to receive a user's selection of the second icon, to receive the user's selection of a Boolean operator in association with the user's section of the second icon, to display a third statement of the rule, display a first link between the third statement and the second statement, where the first link includes an indication of the Boolean operator selected by the user in association with the user's selection of the third icon and where the first link logically links the second statement and the third statement to form a first compound statement, and to display a second link between the first compound statement and the first statement of the rule, where the second link includes an indication of the Boolean operator selected in association with the user's selection of the first icon, and wherein the second link logically links the first compound statement and the first statement of the rule to form a second compound statement.

In another general aspect, a system includes a display configured for displaying graphical information to a user, one or more tangible computer-readable media including machine-executable instructions, and one or more instruction processors configured to execute at least a portion of the machine-executable instructions stored in the tangible computer-readable media. Execution of the instructions causes rendering of a first statement of a rule on the display, rendering of a first icon in association with the first statement on the display. Execution of the instructions also causes determining a user's selection of the first icon by one of the instruction processors, determining the user's selection of a Boolean operator in association with the user's selection of the first icon, rendering a second statement of the rule on the display, and rendering a link between the first statement and the second statement on the display to form a compound statement including the first and second statements, where the link includes an indication of the Boolean operator selected by the user. Execution of the instructions also includes rendering a second icon on the display in association with the second statement, where the second icon is selectable by the user to allow the user to choose a Boolean operator with which the user may link the second statement via the selected Boolean operator to a third statement, and rendering a third icon in association with the compound statement on the display, where the icon is selectable by the user to allow the user to choose a Boolean operator with which the user may link the compound statement via a Boolean operator to a third statement.

Implementations can include one or more of the following features. For example, a first position of an icon relative to a statement in the display can indicate that the icon may be selected by the user to link the statement to another statement, and a second position of the icon relative to a compound statement in the display can indicate that the icon may be selected by the user to link the compound statement to another statement. The first position can be on a first side of the statement and the second position can be on a second side of the compound statement. Representations of the first, second, and third icon in the display can be substantially similar. Execution of the instructions can further cause displaying a fourth icon in association with the first statement, where the fourth icon is selectable by the user to undisplay the first statement. The rule can includes a plurality of eligibility statements and/or a plurality of compliance statements.

Execution of the instructions can further cause displaying a field for inputting a sub-statement of the first statement in the display, receiving input from the user in the field, and, based on the input, displaying in the display a choice of a plurality of sub-statements for selection by the user as the sub-statement of the first statement, and receiving a selection from the user of one of the plurality of sub-statements for use as the sub-statement of the first statement.

Execution of the instructions can further cause receiving a user's selection of the third icon, receiving the user's selection of a Boolean operator in association with the user's selection of the third icon, displaying a third statement of the rule in the display, and displaying a link between the third statement and the compound statement of the first and second statements, where the link includes an indication of the Boolean operator selected by the user that logically links the third statement and the compound statement of the first and second statements, and where the second link logically links the first compound statement and the third statement of the rule to form a second compound statement.

Execution of the instructions can further cause receiving a user's selection of the second icon, receiving the user's selection of a Boolean operator in association with the user's selection of the second icon, displaying a third statement of the rule, and displaying a first link between the third statement and the second statement of the rule, where the first link includes an indication of the Boolean operator selected by the user that logically links the second statement and the second statement to form a first compound statement. A second link between the first compound statement and the first statement of the rule can be displayed, where the second link includes an indication of the Boolean operator selected in association with the user's selection of the first icon, and where the second link logically links the first compound statement and the first statement of the rule to form a second compound statement.

BRIEF DESCRIPTION OF THE DRAWINGS

FIG. 1 is a schematic block diagram of a system for determining the relevance of a URL parameter for identifying a content item referenced by the URL.

FIGS. 5A and 5B are screen shots of a user interface illustrating results of example operations of the system of FIG. 1 to add a rule statement to a compound statement of a rule.

DETAILED DESCRIPTION

Figure 2A:
FIGS. 2A, 2B, 2C, 2D, 2E, 2F, 2G, 2H are screen shots of a user interface illustrating results of example operations of the system of FIG. 1 in which a rule is generated by logically linking a plurality of rule statements.

As described herein, a system can provide a graphical user interface (GUI) through which rules are presented to a user. The user can compose a rule in the GUI by linking together a number of different rule statements with Boolean operators that indicate the logical and hierarchical relationship between the different statements in the rule. An image of an icon associated with a first rule statement displayed in the GUI may be selected by the user to generate a Boolean operator that will be associated with the first rule statement and second rule statement and that will link the first and second rule statements into a compound statement. An image of the icon can also be associated with the compound statement, and selection of this icon can be used to associate and link the compound statement though another Boolean operator with a third statement. An icon can also be associated with the second statement, and selection of this icon can be used to associate and link the second statement though another Boolean operator with a third statement. The logical relationship between the different rule statements of a rule can be displayed in the GUI in a hierarchical structure that illustrates graphically both the hierarchical and logical relationships between the different statements of the rule. In this manner, rules can be quickly and effectively composed within the system because the user is able to understand easily the logical and hierarchical structure of the rule via the GUI.

FIG. 1 illustrates an example system 100 in which embodiments may be implemented (e.g., in a device) to generate rules for use in diagnosis and treatment of patients. The system 100 includes a rule system 102 that may be used, for example, to generate, evaluate, and implement rules for use in the diagnosis and treatment of one or more patients, based at least in part on graphical representations of the rules. Basing generation, evaluation, and implementation on such graphical representations may allow, for example, effective use of a visual perception or recognition of the logical links between individual statements of the of a rule. Consequently, the generation, evaluation, and implementation of rules may be made quickly, effectively, and accurately.

In FIG. 1, the rule system 102 may be used by a user 104. The user 104 may, for example, use the rule system 102 to retrieve pre-determined rule statements, enter new rule statements, generate rules that include multiple statements linked by Boolean operators, and store or retrieve generated rules. The user 104 may generally represent, for example, any person, including, for example, a doctor, a nurse, a physician's assistant, or a medical researcher. The user 104 also may represent someone involved in developing, managing, or implementing rules within the rule system 102, e.g., a software developer with clinical knowledge (or access to clinical knowledge), a database manager, or an information technologies specialist. Even more generally, some or all of various functions or aspects described herein with respect to the user 104 may be performed automatically, e.g., by an appropriately-designed and implemented computing device, or by software agents or other automated techniques.

In the example of FIG. 1, the rule system 102 may be used to provide a user interface 108 on a display device 106, where the user interface may represent, for example, a browser or virtually any type of interactive application that allows for receipt and display of text, graphics, or other types of information. As shown, the user interface 108 may be used to provide graphical representations of statements of a rule in one or more input fields 110. In this context, an input field 110 may be provided in the user interface to allow the user 104 to select a rule statement from a number of pre-determined rule statements, which may be stored in a rule statement database 120.

For example, in one implementation, an input field 110 can provide a drop-down menu of pre-determined rule statements that may be selected by the user, e.g., by activating the drop-down menu though a down-click of a mouse button, scrolling a cursor in the user interface by moving the mouse until the cursor is positioned over a desired rule statement, and then selecting the statement through an up-click of the mouse button. Thus, when the user 104 depresses a mouse button with the cursor positioned over a drop-down menu, a signal may be received by a parameter handler 116 in the rule system, and, in response to the signal, the parameter handler may retrieve one or more pre-determined rule statements from a rule statement database 120 and pass the statements to the display device 106 for display in the user interface. When the user scrolls the cursor over a desired one of the pre-determined rule statements and releases the mouse button, an up-click signal is sent to the parameter handler, causing only the desired rule statement to be displayed in the input field 110.

In another implementation, a user can enter textual input in an input field 110, and based on the input, a parameter handler 116 can retrieve one or more pre-determined rule statements from a rule statement database 120 and pass the statements to the display device 106 for display in the user interface. For example, if the user enters a character string of three letters in the input field 110, the parameter handler 116 may retrieve several pre-determined rule statements from the rule statement database 120, which begin with the three letters of the character string. The several statements can be displayed in the user interface, e.g., in a drop-down menu from which the user may select one of the displayed statements for use in the input field, e.g., as described above.

Rule statements displayed in the user interface 108 can be logically linked to other rule statements that are also displayed in the user interface. For example, a user can select an icon 112 that is associated with a first rule statement, and in association with this selection a Boolean operator can be selected by the user. Thus, in one implementation, an icon 112 that is associated with a first rule statement can be selected by the user. The selection of the icon may be received by the parameter handler 116, which can cause the user interface to display a choice of Boolean operators, e.g., AND or OR, which may be selected by the user to associate with the first rule statement. In another implementation, the user's selection of the icon 112 with a first mouse button may associate an AND operator with the first rule statement, while the user's selection of the icon 112 with a second mouse button may associate an OR operator with the first rule statement. The selection of the Boolean operator by the user can be received by the parameter handler 116, which may cause a second input field 110 to be displayed in the user interface 108 in association with the Boolean operator that is associated with the first rule statement. The user 104 can use the second input field to generate a second rule statement that is logically related to the first rule statement via the Boolean operator. Within the user interface, a link 122 between the first rule statement and the second rule statement can be displayed in response to the logical association between the first statement and the second statement. For example, the link 122 can illustrate whether the first and second statement are linked by an AND or an OR Boolean operator. The parameter handler can cause the link 122 to be displayed in the user interface in response to the association between the first and second rule statements.

The rule system 102 may include, for example, one or more modules, agents, or other software-based applications that may be configured to provide the functionality described herein, and/or related functionality. For example, in FIG. 1, the rule system 102 is illustrated as including a parameter handler 116 that may be configured to receive the one or more inputs from a user, e.g., from the input fields 110 or as a result of mouse clicks or the actions of other pointing or selection devices (e.g., a touch pad or trackball).

Using the received inputs, a user interface ("UI") generator 118 may be configured to determine input fields 110, icons 112, and links 122 associated with one or more rules or rule statements. For example, the graphical display of a rule in the user interface may include one or more rule statements that may be placed in input fields 110, each associated with an image of an icon 112, and which are connected by links 122 that illustrate logical relationships between the statements, and the UI generator 118 may create and position the appropriate user interface objects to provide such a display of a rule. In so doing, for example, the UI generator 118 may normalize or otherwise process the objects of the user interface, in order to display otherwise disparate objects relative to one another.

In generating the one or more user interface objects, the UI generator 118 may access or otherwise utilize a graphical representation database 124. The graphical representation database 124 may include, for example, a database or other type of memory that stores whole or partial templates (or other relevant information) for use in generating user interface objects on the display 106. For example, in some situations the parameter handler 116 may receive a number of user inputs concerning rule statements for inclusion in the rule, which may be associated with, e.g., low- or high-priority statements within the rule and the UI generator may be invoked to display such qualitatively different statements differently in the user interface 108. Thus, in one implementation, a low-priority statement may be displayed on a gray background that is retrieved from graphical representation database 124, while a high-priority statement may be displayed on a blinking yellow or red background that is retrieved from the graphical representation database 124. More generally, the UI generator 118 may access the graphical representations database 124 to determine any useful information in generating user interface objects for the display a rule including rule statements and their logical and hierarchical interrelationships in the user interface 108.

Based on the inputs from the user receive through the user interface 108, a rule generator 117 can compile rules and, for example, analyze the rules for logical consistency. The rule generator 117 may store a rule in a database (e.g., in the rule statement database 120) for later review and approval/rejection by one or more quality assurance reviewers. If a rule is approved it may included in a database of approved rules that can be used to determine diagnoses and treatments.

Also in FIG. 1, the rule system 102 is illustrated as possibly being included within a device 130 that includes one or more processors 126 and one or more memory devices 128. The memory device(s) 128 can provide a machine-readable medium that stores instructions that can be executed by the processor(s) 126 to perform the actions described herein. The device 130 may include, for example, a mobile computing device, such as a personal digital assistant (PDA), or a laptop computer. Of course, virtually any other computing device may be used to implement the rule system 102, such as, for example, a workstation, a desktop computer, a tablet PC or a networked computing system. Of course, in practice, not all of the rule system 102 components need be implemented on a single computing device. For example, the parameter handler 116 may be implemented in part on a first device that is used locally by the user 104, while one or more of the rule statement database 120, the rule generator 117, and the graphical representation database 124 may be stored and/or executed on a remote, networked device(s). In this way, the user 104, who may be operating in the field, e.g., in an office and/or hospital environment, may be relieved of a responsibility to update, manage, or manipulate the contents of the database(s) 120 and 124, or other otherwise modify or update the rule system 102.

FIGS. 2A, 2B, 2C, 2D, 2E, 2F, 2G, 2H are screen shots of a user interface illustrating results of example operations of the system of FIG. 1 in which a rule is generated by logically linking a plurality of rule statements. FIG. 2A illustrates an input bar 201 including example input fields 202a, 202b, 202c from which a user can select sub-statements of a rule statement. For example, the different input fields can represent different categories of information that can be selected by the user to create a rule statement. For example, selecting the "drug" category 202a can allow the user to access pre-determined rule statements in the rule statement database 120 about the allergic reactions to, effects of, recommended dosages, etc. of various drugs. Selecting the "disease" category 202b, e.g., by using a cursor 204 to mouse over or click on, or otherwise selecting the "disease" tab in the user interface can allow the user to access pre-determined rule statements in the rule statement database 120 about various diseases.

Figure 2B:
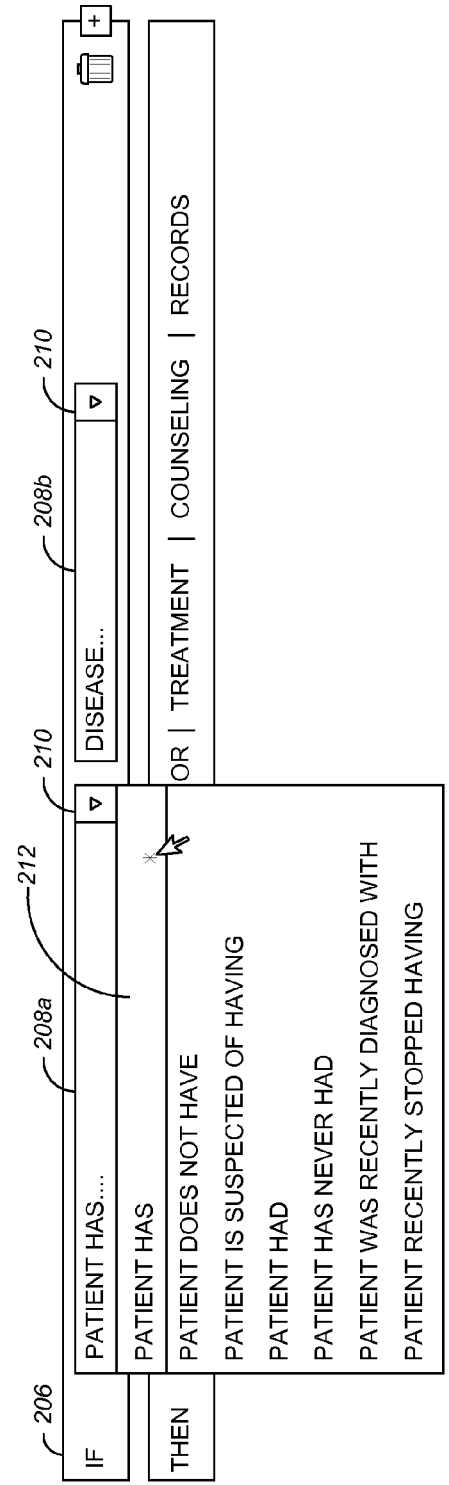

For example, as shown in FIG. 2B, positioning the cursor 204 over the "disease" tab 202b and clicking a mouse button may cause an input bar 206 having one or more input fields 208a and 208b to be displayed in the user interface 108. The input bar can be used by the user 104 to enter information about a rule statement, and the individual input fields 208a and 208b can be used to input sub-statements of the rule, where a sub-statement can be a portion of a statement. For example, a user may position a cursor 204 over, and click on, an icon 210 to activate a drop down menu of suggested inputs for an input field 208a. Then, by clicking on a particular one of the suggested inputs (e.g., "patient has") 212, the particular suggested input can be selected for entry in the input field 208a.

Suggested inputs selected from the rule statement database can be part of a controlled vocabulary for use in rule statements. The controlled vocabulary can be pre-determined by a designer, quality assurance reviewer, or panel of quality assurance reviewers to ensure that language used in rule statements is used consistently among different users of the rules. For example, language of statements in the controlled vocabulary can be chosen to allow a user to distinguish between general "cirrhosis," "cirrhosis of the liver," "primary biliary cirrhosis," "Chronic hepatitis B cirrhosis," and "alcoholic cirrhosis" when referring to cirrhosis in a rule statement.

Figure 2C:
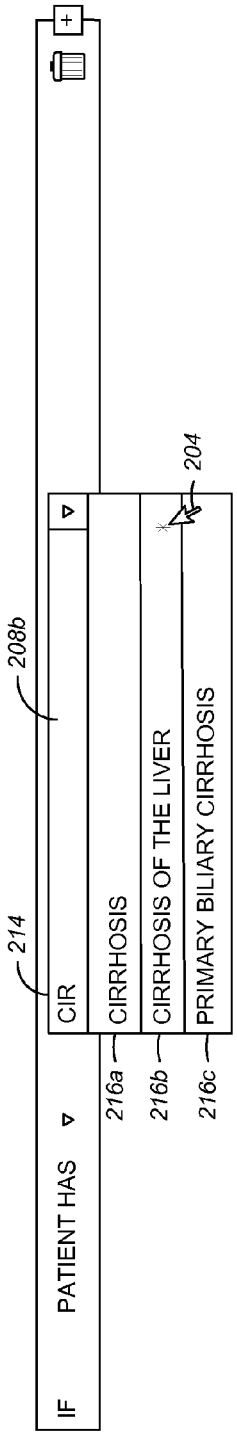
Figure 2D:
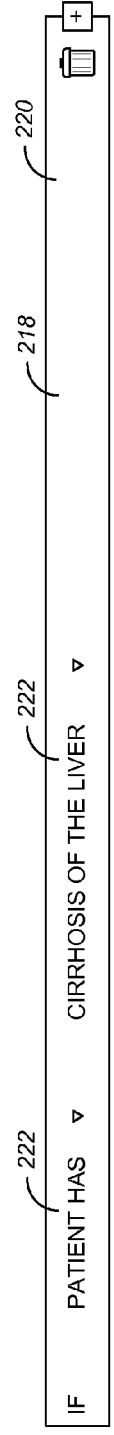

As shown in FIG. 2C, a user may input a character string (e.g., "cir") 214 into an input field 208*b*. The inputted character string 214 can be received by the parameter handler 116 and compared to pre-determined rule statements or sub-statements in the rule statement database 120, and matching entries in the database can be displayed to the user in the user interface 108 as suggested inputs 216*a*, 216*b*, and 216*c* for entry in the input field 208*b*. The user can select a particular one of the suggested inputs 216*b* by mousing over with a cursor 204 and clicking on the particular suggestion. By selecting a particular suggested input, the particular input can be entered into the input bar 206 for the rule sub-statement, and the appearance of the input field 208*b* may change to indicate that the input has been completed. For example, an input field 208*b* may provide a white rectangle to receive input, but after input has been received and finalized in the input field, the field may be shaded to indicate that the input has already been received and additional input is not required. Thus, after the input fields 208*a* and 208*b* of a rule statement have been completed, then, as shown in FIG. 2D, the rule statement 218 can be presented in the user interface 108 in a manner that indicates that additional information is not immediately required. For example, the rule statement can include a uniform background 220 and font 222. The rule statement 220 (i.e., "if patient has cirrhosis of the liver") shown in FIG. 2D can include the sub-statements (i.e., "if patient has" and "cirrhosis of the liver").

Figure 2E:
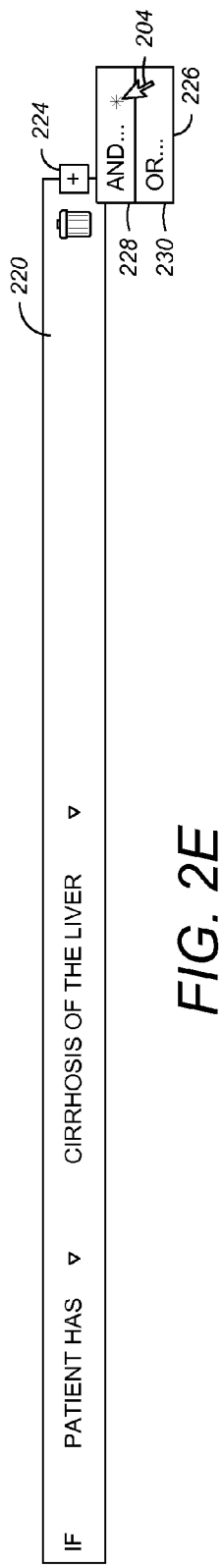

As shown in FIG. 2E, when a first rule statement 220 is displayed in the user interface 108, an icon 224 can be displayed in association with the rule statement. The user 104 can select the icon 224 to initiate the generation of a second rule statement that is linked logically to the first rule statement 220 by a Boolean operation. For example, in one implementation, when the user places a cursor over, or clicks on, the icon 224 a pop-up window 226 can be displayed, from which the user can select one of the Boolean operators, AND 228 or OR 230. For example, once the pop-up window 226 is displayed in the user interface 108, the user can position the cursor over the AND operator 228 and click on a mouse button to logically link the first statement 220 to a second statement through the Boolean AND operator.

Figure 2F:
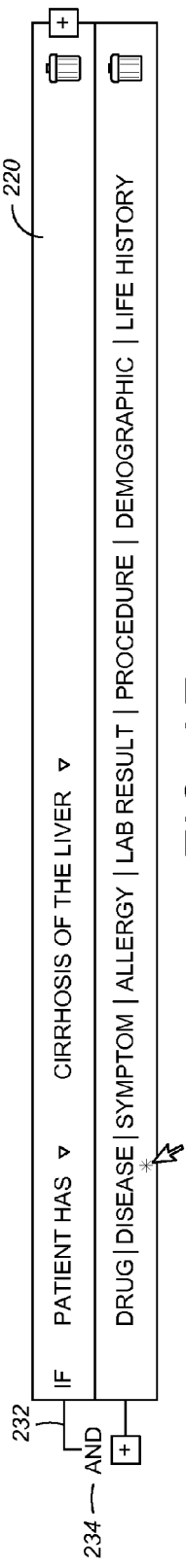

As shown in FIG. 2F, after the user selects a Boolean operator with which to link the first rule statement 220 to a second rule statement, an input bar 201 for creating the second rule statement can be displayed in association with the first rule statement. The association between the first rule statement 220 and the input bar 201 can be illustrated in the user interface 108 by a link 232, which also can show the logical relationship between the first rule statement and the second rule statement. The link 232 can be, for example, a line that connects the first rule statement and the second rule statement (or the input bar that is used to create the second rule statement). The line can include an indication 234 of the logical connection between the first and second rule statements. For example, the indication 234 of the logical connection can be the word "and" to indicated that the two statements are linked by an AND Boolean operator, or the indication 234 could be the word "or" to indicate that the two statements are linked by an OR Boolean operator. In other example implementations, the link between the two statements could be shown by a proximity, color co-ordination, similar font characteristics, etc. of the two statements, and the indication 234 of the logical connection between the two statements could be shown by an icon (e.g., "V" for the OR operator and "Λ" for the AND operator), color co-ordination, similar font characteristics, etc. of the two statements or the link 232 between them. For example, a blue line between the two statements could indicate that the statements are linked logically by a Boolean AND operator, while a red line between the two statements could indicate that the statements are linked logically by a Boolean OR operator.

Figure 2G:
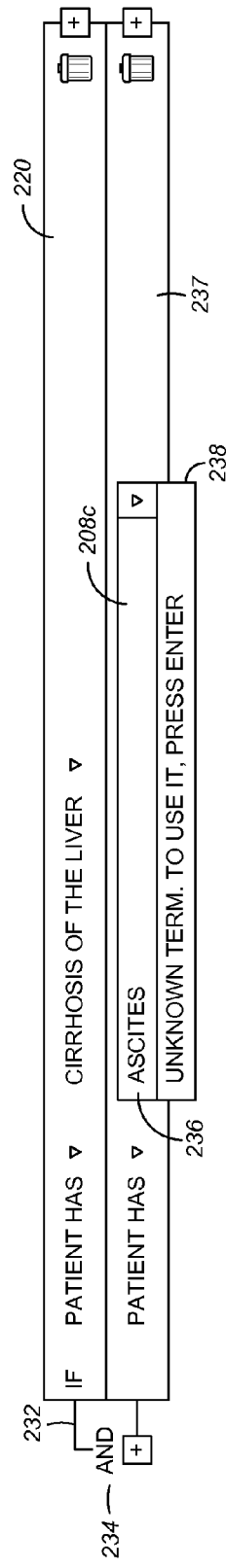

As shown in FIG. 2G, when a user enters a character string 236 in an input field 208*c* of a rule statement 237, which does not correspond to a rule statement or sub-statement stored in the rule statement database 120, then a pop-up window 238 can be displayed in the user interface to indicate that the input does not correspond to any statements or sub-statements in the controlled vocabulary. The pop-up window also can indicate that the character string 236 can be used as input in the rule statement if the user takes additional action to have input the character string 236 as a rule sub-statement (e.g., by pressing an "Enter" key in a user interface). If the user takes such action the character string 236 can be forwarded to a quality assurance reviewer who may determine whether the user's input should be added to the pre-determined rule statement or sub-statements in the rule statement database 120.

Figure 2H:
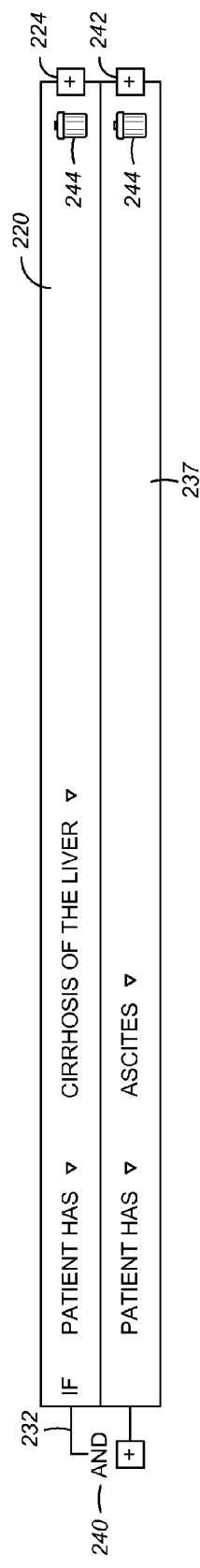

As shown in FIG. 2H, after the user 104 has completed the input for the second rule statement 237, the second rule statement is logically linked to the first rule statement 220 via a Boolean operator. Together the two linked statements form a compound statement. An icon can be associated with the compound statement, and the icon can be selected by the user to link a third statement to the compound statement, in a manner similar to the manner in which icon 224 is selected to link the second rule statement 237 to the first rule statement 220. For example, the icon 240 can be displayed in the user interface 108 adjacent to, or on top of, link 232 to indicated that the icon 240 is associated with the compound statement of the first and second statements. An icon 242 also can be associated with the second rule statement 237, and the icon 242 can be selected to link another rule statement to the second rule statement 237. In one implementation, an image of the icons, 224, 240, and 242 can be substantially similar or identical, such that the user visually understands that the icon can be selected to link another rule statement with the simple rule statement or the compound rule statement with which the image of the icon is associated. For example, a plus sign can be used as the image of the icon 224, 240, 244 in the user interface 108 to indicate to the user that any such icon can be selected to initiate the linking of an additional rule statement to the statement with which the selected icon is associated. An icon 240 associated with a compound rule statement can be distinguished from icon 224 or 242 associated with a simple rule statement 220 or 237, e.g. by the position of the icon in the user interface 108. For example, an icon 240 associated with a compound rule statement can be positioned to the left of the compound rule, while an icon 224 or 242 associated with a simple rule statement 220 or 237 can be positioned to the right of the simple rule statement 220 or 237.

A different image of another icon 244 can associated with the first and/or second rule statement and/or with the compound statement. Selection of this icon 244 can cause the rule statement associated with the selected icon 244 to be deleted from the rule and to be undisplayed in the user interface 108. In one implementation, an image of the icon can resemble a trash can to indicate to the user 104 that selection of the icon 244 will result in the rule statement associated with the selected icon being deleted from the rule and from display in the user interface 108.

Figure 3:
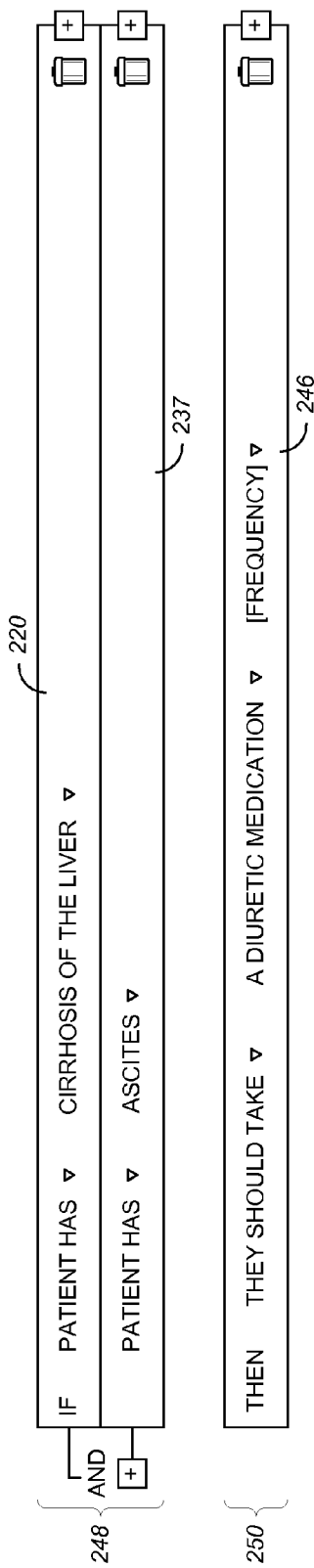
FIG. 3 is a screen shot of user interface illustrating an example rule that includes a plurality of rule statements.

FIG. 3 is a screen shot of a user interface illustrating an example rule that includes a plurality of rule statements. The rule can include one or more rule eligibility statements 220 and 237 that refer to conditions to be met for the rule to be valid (e.g., "patient has cirrhosis of the liver" and "patient has ascites") and one or more compliance statements 246 that refer to consequences of the validity of the of eligibility statements (e.g., "they should take a diuretic medication." Both the eligibility portion 248 of the rule and the compliance portion 250 of the rule can include multiple rule statements that can be linked logically to each other by Boolean operators in compound statements.

After a rule has been defined in the user interface 108 by a user, the user can store the rule in a memory (e.g., a random access memory (RAM) or a non-volatile memory device, such as a hard disk) and then may submit the rule to a quality assurance reviewer or to a panel or reviewers. The reviewer(s) may review the rule in view and may vote or otherwise provide feedback as to whether the rule should be implemented in a rules-based diagnosis and treatment system. Based on the feedback from the quality assurance reviewer(s), a determination can be made as to whether to accept the rule for use by other users in a rules-based diagnosis and treatment system.

Figure 4B:
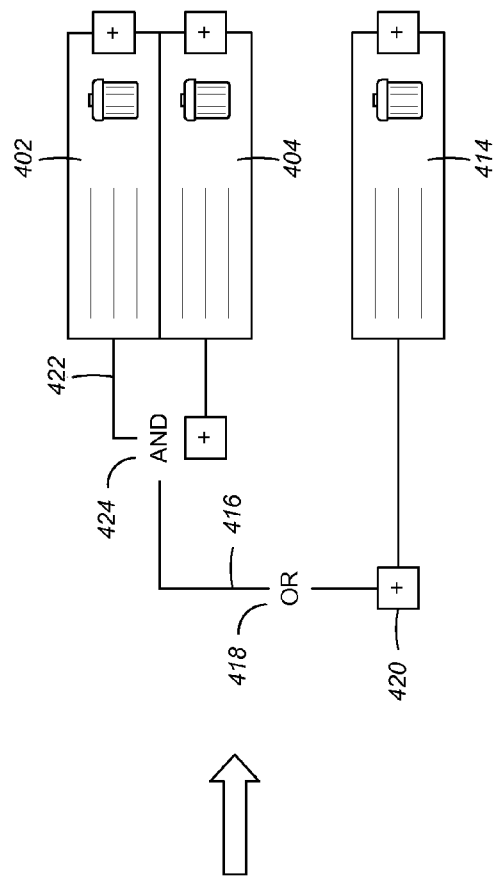
FIGS. 4A and 4B are screen shots of a user interface illustrating results of example operations of the system of FIG. 1 to add a rule statement to a compound statement of a rule.
Figure 4A:
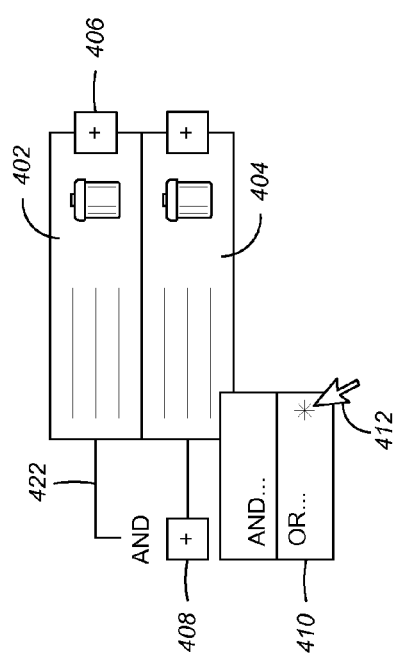

FIGS. 4A and 4B are screen shots of a user interface illustrating results of example operations of the system of FIG. 1 to add a rule statement to a compound statement of a rule. In FIG. 4A a first rule statement 402 and a second rule statement 404 were logically linked together by an AND operator to from a compound statement. For example, a user may have selected an icon 406 associated with the first rule statement 402 to create the second rule statement 404 and link it to the first statement. When the user desires to link the compound statement to a third statement, the user may select an icon 408 associated with the compound statement, and, in association with the selection of the icon 408, the user may selection a Boolean operator with which to link the compound statements and a third statement. For example, selection of the icon 408 may cause the display of a pop-up window 410 that allows the user to select a Boolean operator, AND or OR, e.g., by positioning a cursor 412 over the desired operator and clicking on a mouse. In another implementation, a Boolean operator may be selected by positioning a cursor 412 over the icon 408 and clicking on a first mouse button to select an AND operator or clicking on a second mouse button to select an OR operator.

As shown in FIG. 4B, selecting a Boolean operator (e.g., the OR operator) based on a selection of the icon 408 may cause an input bar to be displayed in the user interface and in which the user can create a third rule statement 414. The third statement 414 can be linked to the compound statement that is composed of the first statement 402 and the second statement 404, and the link between the third rule statement 414 and the compound statement can be illustrated in the user interface by a link 416 (e.g., a line between the compound statement an the third statement). The link 416 can be associated with an indication of 418 of the Boolean operator that logically links the third statement with the compound statement. In this manner, another compound statement can be created between the third rule statement and the compound statement that includes the first and second compound statements 402 and 414. An icon 420 can be associated with this second compound rule statement, and the icon can be used to logically link the second compound statement to a fourth rule statement.

In this manner, the logical and hierarchical relationships between different statements in a rule can be quickly and easily understood by a user from the graphical depiction of the rule statements and their local relationships in the user interface 108. For example, as shown the FIG. 4B, the hierarchical relationships between rule statements 402, 404, and 414 can be understood from the tree structure illustrated by the links 416 and 422, and the logical links between the different rule statements can be seen from the indications 418 and 424 of the Boolean operators that connect the different rule statements.

FIGS. 5A and 5B are screen shots of a user interface illustrating results of example operations of the system of FIG. 1 to add a rule statement to a compound statement of a rule. In FIG. 5A a first rule statement 502 and a second rule statement 504 were logically linked together by an AND operator to from a compound statement. For example, a user may have selected an icon 506 associated with the first rule statement 502 to create the second rule statement 504 and link it to the first statement. The link 503 between the first and second statements can be illustrated by a line between the first and second statements, and an icon 505 can be associated with the link 503 to provide an indication of the logical connection between the first and second statements. When the user desires to link the second statement 504 to a third statement, the user may select an icon 508 associated with the second statement. Selection of the icon 508 may cause the display of a pop-up window 510 that allows the user to select a Boolean operator, AND or OR, e.g. by positioning a cursor 512 over the desired operator in the pop-up window 510 and clicking on a mouse.

As shown in FIG. 5B, selecting a Boolean operator (e.g., the OR operator) in association with a selection of the icon 508 may cause an input bar to be displayed in the user interface and in which the user can create a third rule statement 514. The third statement 514 can be linked to the second statement 504 to form a compound statement composed of the second statement 504 and the third statement 514, and the link between the third rule statement 514 and the second statement can be illustrated in the user interface by a link 516 (e.g., a line between the second statement an the third statement). The link 516 can be associated with an indication of 518 of the Boolean operator that logically links the second statement with the third statement. The link 503 between the first rule statement 502 and the second rule statement 504 is maintained in the user interface after the third rule statement 514 is added. However, after the third rule statement 514 is linked to the second rule statement 504, the link 503 is modified to link the compound statement of second and third statements 504 and 514 to the first statement 502.

Thus, as shown in FIG. 4 and FIG. 5, the result of adding a third rule statement to an existing compound statement, can depend on whether the third rule statement was added in response to selecting an icon associated with the compound statement or associated with one of the component statements of the compound statement. For example, as shown in FIGS. 4A and 4B, by selecting an icon 408 associated with the compound statement, the final statement ((First Statement AND Second Statement) OR Third Statement) is produced. In contrast, as shown in FIGS. 5A and 5B, by selecting an icon 508 associated with the second statement 504, the final statement, (First Statement AND (Second Statement OR Third Statement)) is produced. The two final compound rule statements, shown in FIG. 4 and FIG. 5 are not equivalent because of the associative properties of Boolean logic, which thus illustrates how different icons in the user interface 108 can be selected to create different compound rule statements. Therefore, the icons associated with individual and compound rule statements displayed in the user interface 108 can be used to build up complex rules in the user interface 108 using a hierarchical structure (e.g., a tree structure) that also illustrates the logical connections between different rule statements.

Figure 6:
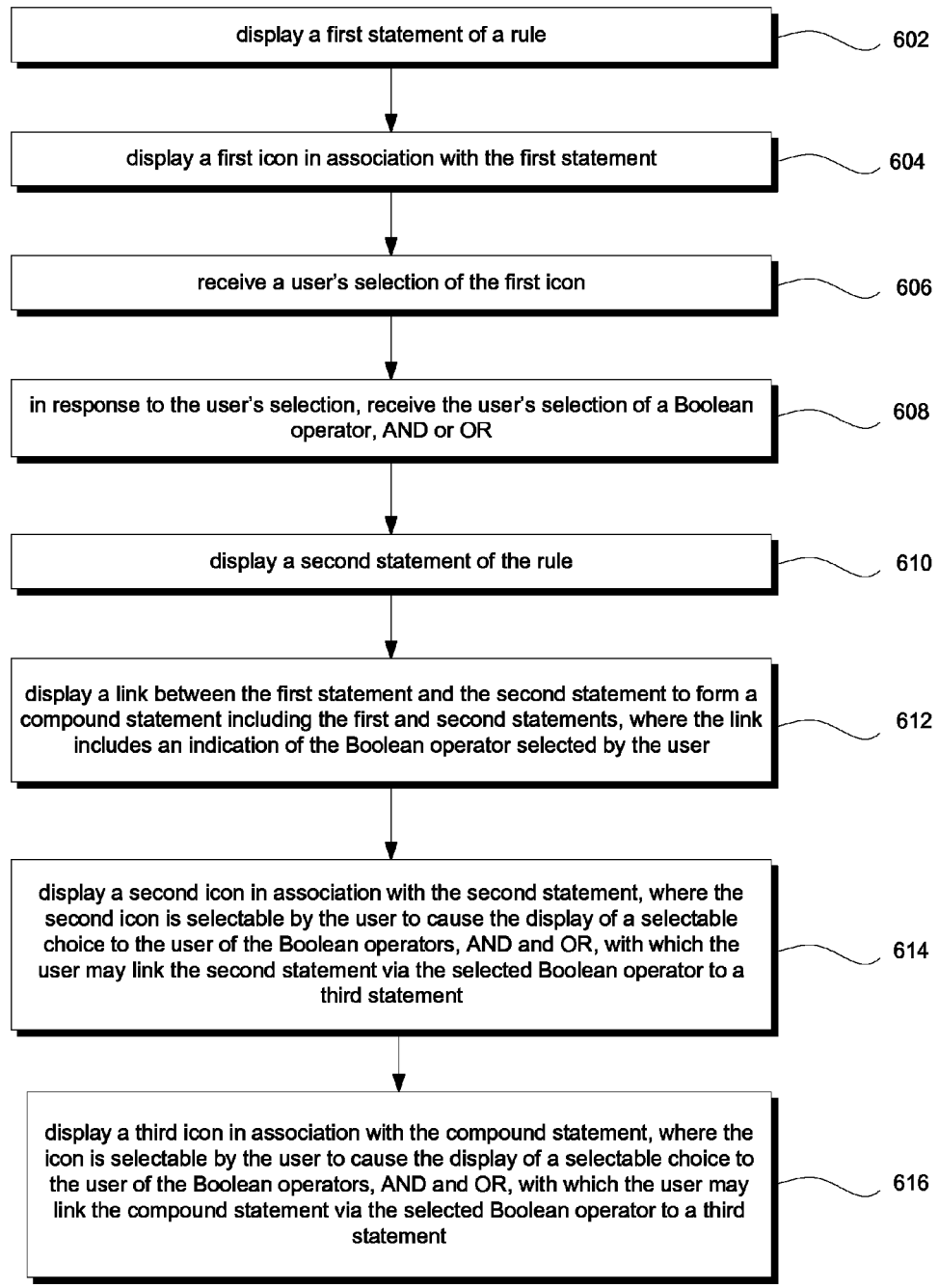
FIG. 6 illustrates an operational flow representing example operations related to display of a rule in a user interface.

FIG. 6 illustrates an operational flow 600 representing example operations related to display of a rule in a user interface. In FIG. 6 discussion and explanation may be provided with respect to the above-described examples of FIGS. 1-5, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 600 moves to a display operation 602, where a first statement of a rule can be displayed. For example, the UI generator 118 of the rule system 102 may cause the first statement of the rule to be displayed in the user interface 108 on the display device 106. In another display operation 604, a first icon may be displayed in association with the first statement. For example, the UI generator 118 may cause an icon 224, 406, or 506 to be displayed in association with a first statement 220, 402, or 502. The association of the icon with the first rule statement may be illustrated in the user interface through a proximity with which positions of the icon and the first rule statement are presented, through a color-coordination, through a GUI object connecting the icon with the first rule statement, or any other association between the icon and the first rule statement.

In a receiving operation 606, a user's selection of the first icon may be received. For example, a user may select a first icon 224, 406, or 506 by scrolling a cursor over the icon, as displayed in the use interface 108, and clicking on a pointing device (e.g., a mouse). The selection of the icon in the user interface can be transmitted to a parameter handler 116 in the rule system 102, where it is received and processed by the parameter handler and other components of the rule system. In particular, in another receiving operation 608, in association with the user's selection of the first icon 224, 406, or 506, a user's selection of a Boolean operator, AND or OR, can be received. For example, when the user selects the icon the user may be prompted (e.g., by the display of a pop-up window 226) to select a Boolean operator. In another implementation, the user may select the icon with a left mouse click to select an AND Boolean operator, and the user may select the icon with a right mouse click to select an OR Boolean operator. Thus, the selection of such a Boolean operator may be received (e.g., by the parameter handler 116) as a consequence of the user's selection of the first icon.

In another display operation 610, a second statement of the rule can be displayed. For example, the UI generator 118 of the rule system 102 may cause the second statement of the rule to be displayed in the user interface 108 along with the first rule statement. In another display operation 612, a link between the first statement and the second statement can be displayed to form a compound statement that includes the first and second statements. In addition, the link can include an indication of the Boolean operator selected by the user. For example, the UI generator may cause the display of a link 232, 422, or 503 between the first and second rule statements, and the link can include an indication 424 or the Boolean operator selected by the user. The link may be displayed in the user interface along with the first and second rule statement to illustrate a hierarchical relationship between the first and second statements. For example, in a tree structure, the link may indicate whether the statements have a sibling or parent-child relationship. The indication of the Boolean operator may illustrate a logical link between the first and second rule statements, i.e., whether they are related though an AND or an OR operation in a Boolean logic of the rule.

In another display operation 614, a second icon may be displayed in association with the second statement, where the second icon is selectable by the user to cause the display of a selectable choice to the user of Boolean operators (e.g., AND and OR), with which the user may link the second statement via the selected Boolean operator to a third statement. For example, the UI generator 118 of the rule system 102 may cause a second icon 508 to be displayed in the user interface 108 in association with the second rule statement 504. As shown in FIGS. 5A and 5B, the second icon 508 can be selected by the user to cause the display of a selectable choice of Boolean operators (e.g., as displayed in pop-up window 510). The user may choose one of these Boolean operators to create a link between the second statement 504 and a third statement 514.

In another display operation 616, a third icon may be displayed in association with a compound statement, where the third icon is selectable by the user to cause the display of a selectable choice to the user of the Boolean operators (e.g., AND and OR) with which the user may link the compound statement via the selected Boolean operator to a third statement. For example, the UI generator 118 of the rule system 102 may cause a third icon 408 to be displayed in the user interface 108 in association with the compound statement that includes the first rule statement 402 and the second rule statement 404. As shown in FIGS. 4A and 4B, the third icon 408 can be selected by the user to cause the display of a selectable choice of Boolean operators (e.g., as displayed in pop-up window 410). The user may choose one of these Boolean operators to create a link between the compound statement and a third statement 414.

Figure 7:
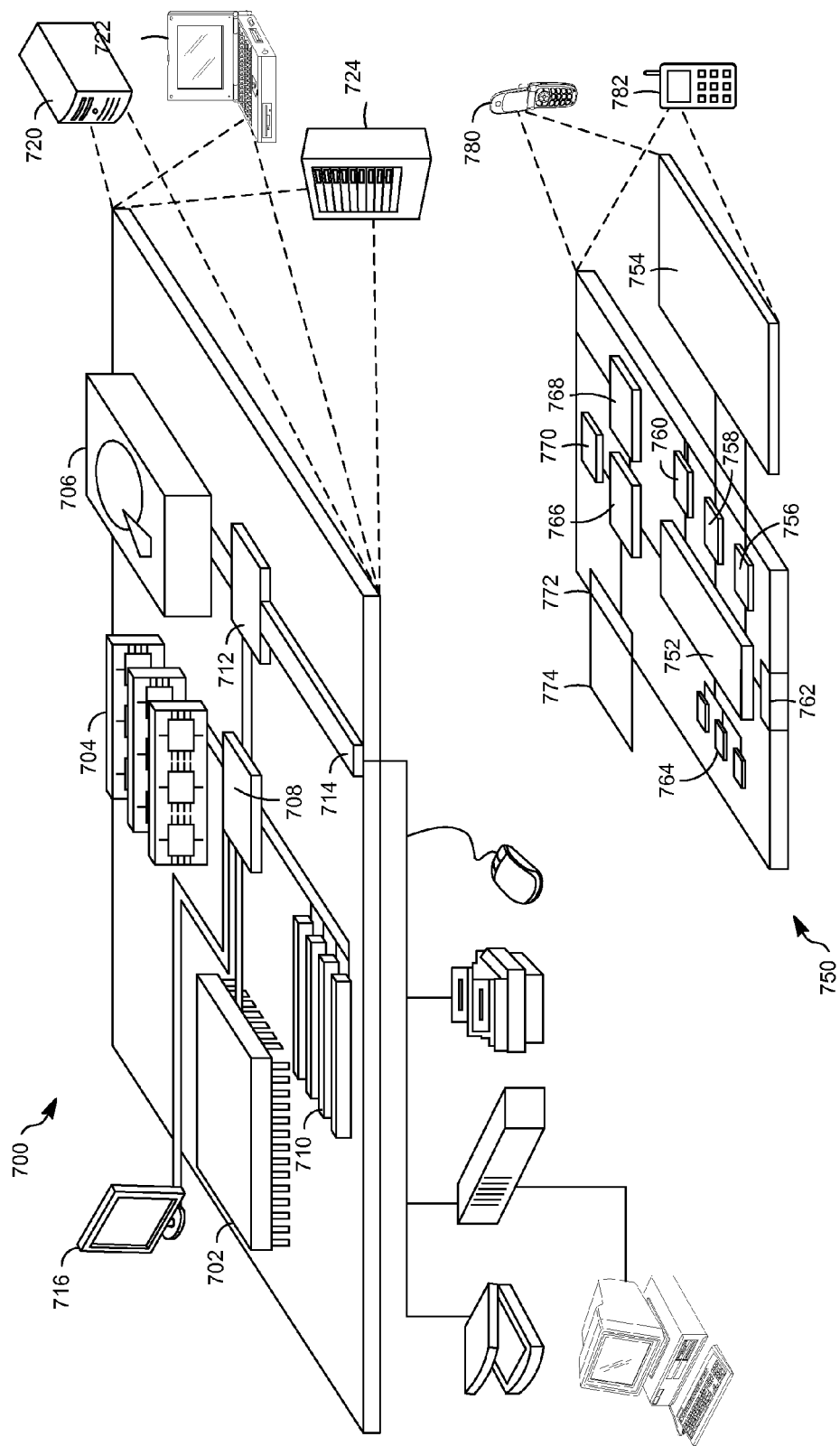
FIG. 7 shows an example of a computer device and a mobile computer device, which may be used with the techniques described herein.

FIG. 7 shows an example of a generic computer device 700 and a generic mobile computer device 750, which may be used with the techniques described herein. Computing device 700 is intended to represent various forms of digital computers, such as laptops, desktops, workstations, personal digital assistants, servers, blade servers, mainframes, and other appropriate computers. Computing device 750 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 700 includes a processor 702, memory 704, a storage device 706, a high-speed interface 708 connecting to memory 704 and high-speed expansion ports 710, and a low speed interface 712 connecting to low speed bus 714 and storage device 706. Each of the components 702, 704, 706, 708, 710, and 712, are interconnected using various busses, and may be mounted on a common motherboard or in other manners as appropriate. The processor 702 can process instructions for execution within the computing device 700, including instructions stored in the memory 704 or on the storage device 706 to display graphical information for a GUI on an external input/output device, such as display 716 coupled to high speed interface 708. In other implementations, multiple processors and/or multiple buses may be used, as appropriate, along with multiple memories and types of memory. Also, multiple computing devices 700 may be connected, with each device providing portions of the necessary operations (e.g., as a server bank, a group of blade servers, or a multi-processor system).

The memory 704 stores information within the computing device 700. In one implementation, the memory 704 is a volatile memory unit or units. In another implementation, the memory 704 is a non-volatile memory unit or units. The memory 704 may also be another form of computer-readable medium, such as a magnetic or optical disk.

The storage device 706 is capable of providing mass storage for the computing device 700. In one implementation, the storage device 706 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 704, the storage device 706, or memory on processor 702.

The high speed controller 708 manages bandwidth-intensive operations for the computing device 700, while the low speed controller 712 manages lower bandwidth-intensive operations. Such allocation of functions is exemplary only. In one implementation, the high-speed controller 708 is coupled to memory 704, display 716 (e.g., through a graphics processor or accelerator), and to high-speed expansion ports 710, which may accept various expansion cards (not shown). In the implementation, low-speed controller 712 is coupled to storage device 706 and low-speed expansion port 714. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 700 may be implemented in a number of different forms, as shown in the figure. For example, it may be implemented as a standard server 720, or multiple times in a group of such servers. It may also be implemented as part of a rack server system 724. In addition, it may be implemented in a personal computer such as a laptop computer 722. Alternatively, components from computing device 700 may be combined with other components in a mobile device (not shown), such as device 750. Each of such devices may contain one or more of computing device 700, 750, and an entire system may be made up of multiple computing devices 700, 750 communicating with each other.

Computing device 750 includes a processor 752, memory 764, an input/output device such as a display 754, a communication interface 766, and a transceiver 768, among other components. The device 750 may also be provided with a storage device, such as a microdrive or other device, to provide additional storage. Each of the components 750, 752, 764, 754, 766, and 768, are interconnected using various buses, and several of the components may be mounted on a common motherboard or in other manners as appropriate.

The processor 752 can execute instructions within the computing device 750, including instructions stored in the memory 764. The processor may be implemented as a chipset of chips that include separate and multiple analog and digital processors. The processor may provide, for example, for coordination of the other components of the device 750, such as control of user interfaces, applications run by device 750, and wireless communication by device 750.

Processor 752 may communicate with a user through control interface 758 and display interface 756 coupled to a display 754. The display 754 may be, for example, a TFT LCD (Thin-Film-Transistor Liquid Crystal Display) or an OLED (Organic Light Emitting Diode) display, or other appropriate display technology. The display interface 756 may comprise appropriate circuitry for driving the display 754 to present graphical and other information to a user. The control interface 758 may receive commands from a user and convert them for submission to the processor 752. In addition, an external interface 762 may be provide in communication with processor 752, so as to enable near area communication of device 750 with other devices. External interface 762 may provide, for example, for wired communication in some implementations, or for wireless communication in other implementations, and multiple interfaces may also be used.

The memory 764 stores information within the computing device 750. The memory 764 can be implemented as one or more of a computer-readable medium or media, a volatile memory unit or units, or a non-volatile memory unit or units. Expansion memory 774 may also be provided and connected to device 750 through expansion interface 772, which may include, for example, a SIMM (Single In Line Memory Module) card interface. Such expansion memory 774 may provide extra storage space for device 750, or may also store applications or other information for device 750. Specifically, expansion memory 774 may include instructions to carry out or supplement the processes described above, and may include secure information also. Thus, for example, expansion memory 774 may be provide as a security module for device 750, and may be programmed with instructions that permit secure use of device 750. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 764, expansion memory 774, or memory on processor 752, that may be received, for example, over transceiver 768 or external interface 762.

Device 750 may communicate wirelessly through communication interface 766, which may include digital signal processing circuitry where necessary. Communication interface 766 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 768. In addition, short-range communication may occur, such as using a Bluetooth, WiFi, or other such transceiver (not shown). In addition, GPS (Global Positioning System) receiver module 770 may provide additional navigation- and location-related wireless data to device 750, which may be used as appropriate by applications running on device 750.

Device 750 may also communicate audibly using audio codec 760, which may receive spoken information from a user and convert it to usable digital information. Audio codec 760 may likewise generate audible sound for a user, such as through a speaker, e.g., in a handset of device 750. Such sound may include sound from voice telephone calls, may include recorded sound (e.g., voice messages, music files, etc.) and may also include sound generated by applications operating on device 750.

The computing device 750 may be implemented in a number of different forms, as shown in the figure. For example, it may be implemented as a cellular telephone 780. It may also be implemented as part of a smart phone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer-implemented method comprising:
displaying a first statement of a rule, wherein the first statement includes a plurality of sub-statements selected by a user from a controlled vocabulary of suggested sub-statements;
displaying a second statement of the rule, wherein the second statement includes a plurality of sub-statements selected by a user from the controlled vocabulary of suggested sub-statements;
displaying a first instance of a selectable icon in association with the first statement and in a first position, relative to the first statement, wherein the first position of the icon, relative to the first statement, indicates that the first instance of the icon is selectable by the user to link the first statement to a new statement of the rule and is not selectable to link a compound statement of the rule that includes the first and second statements to a new statement of the rule;
displaying a second instance of the selectable icon in association with the second statement and in the first position, relative to the second statement, wherein the first position of the icon, relative to the second statement, indicates that the second instance of the icon is selectable by the user to link the second statement to a new statement of the rule and is not selectable to link the compound statement of the rule that includes the first and second statements to a new statement of the rule;
displaying a first link between the first statement and the second statement to visually indicate a first compound statement of the rule including the first and second statements, wherein the first link includes a third instance of the selectable icon and wherein the link includes an indication of a first selected Boolean operator selected by the user in response to a selection of the first instance of the selectable icon by the user and wherein the Boolean operator logically links the first and second statements of the rule, wherein the third instance of the selectable icon is displayed in a second position, relative to the compound statement, which second position is different from the first position and which indicates that the third instance of the icon is selectable by the user to link the compound statement to a new statement of the rule and is not selectable to link the first or second statements to a new statement of the rule;
in response to a user's selection of the first or second instance of the icon associated with the first or second rule statement:
displaying a plurality of Boolean operators in association with the respective statement of the rule;
receiving the user's selection of one of the displayed Boolean operators;
in response to the user's selection of the second selected Boolean operator:
displaying a third statement of the rule that includes a plurality of sub-statements selected by the user from the controlled vocabulary of suggested statements; and
displaying a second link between the third statement and the respective statement to visually indicate a second compound statement of the rule including the third statement and the respective statement, wherein the second link includes a fourth instance of the selectable icon and wherein the second link includes an indication of the second selected Boolean operator that was selected, wherein the second selected Boolean operator logically links the first and second statements of the rule;

displaying a third link between the second compound statement and the first or second rule statement, whichever one was not associated with the instance of the icon selected by the user, to visually indicate a third compound statement of the rule including the second compound statement and the first or second rule statement, whichever one was not associated with the instance of the icon selected by the user, wherein the third link includes the third instance of the selectable icon and an indication of the first selected Boolean operator; and in response to a user's selection of the third instance of the selectable icon associated with the first compound statement:

displaying a plurality of Boolean operators in association with the first compound statement of the rule;

receiving the user's selection of one of the displayed Boolean operators;

in response to the user's selection of the third selected Boolean operator:

displaying a fourth statement of the rule that includes a plurality of sub-statements selected by the user from the controlled vocabulary of suggested statements; and displaying a fourth link between the fourth statement and the first compound statement to visually indicate a third compound statement of the rule including the fourth statement and the first compound statement, wherein the fourth link includes a fifth instance of the selectable icon and wherein the fourth link includes an indication of the third selected Boolean operator, wherein the third selected Boolean operator logically links the first compound statement and fourth statement of the rule.

2. The method of claim 1, wherein representations of the first, second, third, fourth, and fifth instances of the selectable icon are identical.

3. The method of claim 1, wherein the controlled vocabulary of suggested sub-statements refers to a medical condition or treatment of a patient.

4. The method of claim 1,
wherein a position of the third link relative to the second link indicates a hierarchical relationship between the second compound statement and the third rule statement, which obeys associative properties of the Boolean operations associated with the third and second links, and
wherein a position of the fourth link relative to the first link indicates a hierarchical relationship between the first compound statement and the fourth rule statement, which obeys associative properties of the Boolean operations associated with the fourth and first links.

5. A computer program product tangibly embodied in a non-transitory machine-readable medium and including executable instructions that, when executed, are configured to cause one or more data processing apparatuses to:

display a first statement of a rule, wherein the first statement includes a plurality of sub-statements selected by a user from a controlled vocabulary of suggested sub-statements;

display a second statement of the rule, wherein the second statement includes a plurality of sub-statements selected by a user from the controlled vocabulary of suggested sub-statements;

display a first instance of a selectable icon in association with the first statement wherein the first instance of the selectable icon is displayed in a first position, relative to the first statement, which first position indicates that the first instance of the icon is selectable by the user to link the first statement to a new statement of the rule and not to link the compound statement to a new statement of the rule;

display a second instance of the selectable icon in association with the second statement, wherein the second instance of the selectable icon is displayed in the first position, relative to the second statement, which first position indicates that the second instance of the icon is selectable by the user to link the second statement to a new statement of the rule and not to link the compound statement to a new statement of the rule;

display a first link between the first statement and the second statement to visually indicate a first compound statement of the rule including the first and second statements, wherein the first link includes a third instance of the selectable icon and wherein the link includes an indication of a first selected Boolean operator selected by the user in response to a selection of the first instance of the selectable icon by the user and wherein the Boolean operator logically links the first and second statements of the rule, wherein the third instance of the selectable icon is displayed in a second position, relative to the compound statement, which second position indicates that the third instance of the icon is selectable by the user to link the compound statement to a new statement of the rule and not to link the first or second statement to a new statement of the rule;

in response to a user's selection of the first or second instance of the icon associated with the first or second rule statement:

display a plurality of Boolean operators in association with the respective statement of the rule;

receive the user's selection of one of the displayed Boolean operators;

in response to the user's selection of the second selected Boolean operator:

display a third statement of the rule that includes a plurality of sub-statements selected by the user from the controlled vocabulary of suggested statements;

display a second link between the third statement and the respective statement to visually indicate a second compound statement of the rule including the third statement and the respective statement, wherein the second link includes a fourth instance of the selectable icon and wherein the second link includes an indication of the second selected Boolean operator that was selected, wherein the second selected Boolean operator logically links the first and second statements of the rule; and display a third link between the second compound statement and the first or second rule statement, whichever one was not associated with the instance of the icon selected by the user, to visually indicate a third compound statement of the rule including the second compound statement and the first or second rule statement, whichever one was not associated with the instance of the icon selected by the user, wherein the third link includes the third instance of the selectable icon and an indication of the first selected Boolean operator; and in response to a user's selection of the third instance of the selectable icon associated with the first compound statement:

display a plurality of Boolean operators in association with the first compound statement of the rule;

receive the user's selection of one of the displayed Boolean operators;

in response to the user's selection of the third selected Boolean operator:

display a fourth statement of the rule that includes a plurality of sub-statements selected by the user from the controlled vocabulary of suggested statements; and display a fourth link between the fourth statement and the first compound statement to visually indicate a third compound statement of the rule including the fourth statement and the first compound statement, wherein the fourth link includes a fifth instance of the selectable icon and wherein the fourth link includes an indication of the third selected Boolean operator, wherein the third selected Boolean operator logically links the first compound statement and fourth statement of the rule.

6. The computer program product of claim 5, wherein the plurality of Boolean operators include the Boolean operators, AND and OR.

7. The computer program product of claim 5, wherein representations of the first, second, third, fourth, and fifth instances of the selectable icon are identical.

8. The computer program product of claim 5, wherein the controlled vocabulary of suggested sub-statements refers to a medical condition or treatment of a patient.

9. The computer program product of claim 5, wherein a position of the third link relative to the second link indicates a hierarchical relationship between the second compound statement and the third rule statement, which obeys associative properties of the Boolean operations associated with the third and second links, and wherein a position of the fourth link relative to the first link indicates a hierarchical relationship between the first compound statement and the fourth rule statement, which obeys associative properties of the Boolean operations associated with the fourth and first links.

10. A system comprising:

a display configured for displaying graphical information to a user;

one or more tangible computer-readable media including machine-executable instructions; and one or more instruction processors configured to execute at least a portion of the machine-executable instructions stored in the tangible computer-readable media, wherein execution of the instructions causes:

displaying a first statement of a rule, wherein the first statement includes a plurality of sub-statements selected by a user from a controlled vocabulary of suggested sub-statements;

displaying a second statement of the rule, wherein the second statement includes a plurality of sub-statements selected by a user from the controlled vocabulary of suggested sub-statements;

displaying a first instance of a selectable icon in association with the first statement, wherein the first instance of the selectable icon is displayed in a first position, relative to the first statement, which first position indicates that the first instance of the icon is selectable by the user to link the first statement to a new statement of the rule and not to link the compound statement to a new statement of the rule;

displaying a second instance of the selectable icon in association with the second statement, wherein the second instance of the selectable icon is displayed in the first position, relative to the second statement, which first position indicates that the second instance of the icon is selectable by the user to link the second statement to a new statement of the rule and not to link the compound statement to a new statement of the rule;

displaying a first link between the first statement and the second statement to visually indicate a first compound statement of the rule including the first and second statements, wherein the first link includes a third instance of the selectable icon and wherein the link includes an indication of a first selected Boolean operator selected by the user in response to a selection of the first instance of the selectable icon by the user and wherein the Boolean operator logically links the first and second statements of the rule, wherein the third instance of the selectable icon is displayed in a second position, relative to the compound statement, which second position indicates that the third instance of the icon is selectable by the user to link the compound statement to a new statement of the rule and not to link the first or second statement to a new statement of the rule;

in response to receiving a user's selection of the first or second instance of the icon associated with the first or second rule statement:

displaying a plurality of Boolean operators in association with the respective statement of the rule;

receiving the user's selection of one of the displayed Boolean operators;

in response to the user's selection of the second selected Boolean operator:

displaying a third statement of the rule that includes a plurality of sub-statements selected by the user from the controlled vocabulary of suggested statements;

displaying a second link between the third statement and the respective statement to visually indicate a second compound statement of the rule including the third statement and the respective statement, wherein the second link includes a fourth instance of the selectable icon and wherein the second link includes an indication of the second selected Boolean operator that was selected, wherein the second selected Boolean operator logically links the first and second statements of the rule; and displaying a third link between the second compound statement and the first or second rule statement, whichever one was not associated with the instance of the icon selected by the user, to visually indicate a third compound statement of the rule including the second compound statement and the first or second rule statement, whichever one was not associated with the instance of the icon selected by the user, wherein the third link includes the third instance of the selectable icon and an indication of the first selected Boolean operator; and in response to a user's selection of the third instance of the selectable icon associated with the first compound statement:
   displaying a plurality of Boolean operators in association with the first compound statement of the rule;
   receiving the user's selection of one of the displayed Boolean operators;
   in response to the user's selection of the third selected Boolean operator:
      displaying a fourth statement of the rule that includes a plurality of sub-statements selected by the user from the controlled vocabulary of suggested statements; and
      displaying a fourth link between the fourth statement and the first compound statement to visually indicate a third compound statement of the rule including the fourth statement and the first compound statement, wherein the fourth link includes a fifth instance of the selectable icon and wherein the fourth link includes an indication of the third selected Boolean operator, wherein the third selected Boolean operator logically links the first compound statement and fourth statement of the rule.

11. The system of claim 10, wherein a first position of an instance of the selectable icon relative to a statement indicates that the instance of the icon may be selected by the user to link the statement to another statement, and wherein a second position of the instance of the icon relative to a compound statement indicates that the icon may be selected by the user to link the compound statement to another statement.

12. The system of claim 11, wherein the first position is on a first side of the statement and wherein the second position is on a second side of the compound statement.

13. The system of claim 11, wherein execution of the instructions further causes displaying a sixth instance of the icon in association with the first statement, wherein the sixth instance of the icon is selectable by the user to undisplay the first statement.

14. The system of claim 11, wherein the rule includes a plurality of eligibility statements.

15. The system of claim 11, wherein the rule includes a plurality of compliance statements.

16. The system of claim 10, wherein representations of the first, second, third, fourth, and fifth instances of the selectable icon are identical.

17. The system of claim 10, wherein the controlled vocabulary of suggested sub-statements refers to a medical condition or treatment of a patient.

18. The system of claim 10,
   wherein a position of the third link relative to the second link indicates a hierarchical relationship between the second compound statement and the third rule statement, which obeys associative properties of the Boolean operations associated with the third and second links, and
   wherein a position of the fourth link relative to the first link indicates a hierarchical relationship between the first compound statement and the fourth rule statement, which obeys associative properties of the Boolean operations associated with the fourth and first links.

\* \* \* \* \*